United States Patent [19]

Schwartz

[11] Patent Number: 5,320,527
[45] Date of Patent: Jun. 14, 1994

[54] DENTAL ARCH FORM

[76] Inventor: Robert Schwartz, 1271 Westfield Ave., Rahway, N.J. 07065

[21] Appl. No.: 829,944

[22] Filed: Feb. 3, 1992

[51] Int. Cl.⁵ .......................... A61C 1/14; A61C 3/04; A61C 11/00
[52] U.S. Cl. ...................... 433/49; 433/55; 433/59
[58] Field of Search ............... 433/49, 53, 55, 59, 433/68, 69, 72, 196, 213

[56] References Cited

U.S. PATENT DOCUMENTS

| | | |
|---|---|---|
| 1,079,540 | 11/1913 | Clapp et al. |
| 1,518,075 | 12/1924 | Kesling. |
| 2,107,181 | 2/1938 | Guyton. |
| 2,656,603 | 10/1953 | Brassie. |
| 2,754,589 | 7/1956 | Highkin. |
| 2,817,900 | 12/1957 | Glasser. |
| 3,335,495 | 8/1967 | Wichner. |
| 3,465,443 | 9/1969 | Schwartz et al. ........ 433/60 |
| 3,482,312 | 12/1969 | Smith ...................... 433/69 |
| 3,576,075 | 4/1971 | Scott ..................... 433/213 X |
| 3,581,398 | 6/1971 | Thomas. |
| 3,694,919 | 10/1972 | Lee et al. ................ 433/55 |
| 3,875,665 | 4/1975 | Weissman. |
| 3,890,710 | 6/1975 | Jaeger. |
| 3,913,230 | 10/1975 | Weiss ..................... 433/49 |
| 4,083,114 | 4/1978 | Acevedo. |
| 4,122,606 | 10/1978 | Roman. |
| 4,133,110 | 1/1979 | Bernstein et al. |
| 4,155,163 | 5/1979 | Schwartz ................. 433/56 |
| 4,265,619 | 5/1981 | Lucki et al. |
| 4,278,426 | 7/1981 | Schwartz ................. 433/54 |
| 4,460,338 | 7/1984 | Mercer et al. |
| 4,551,098 | 11/1985 | Blair. |
| 4,571,186 | 2/1986 | Pipko. |
| 4,681,542 | 7/1987 | Baum. |
| 4,762,490 | 8/1988 | Ludwigs. |
| 4,780,082 | 10/1988 | Schwartz. |
| 4,812,118 | 3/1989 | Creekmore. |
| 4,906,186 | 3/1990 | France, Jr. |
| 4,997,370 | 3/1991 | Mayclin. |

FOREIGN PATENT DOCUMENTS

| | | | |
|---|---|---|---|
| 845238 | 7/1952 | Fed. Rep. of Germany | 433/196 |
| 3906982 | 6/1990 | Fed. Rep. of Germany | 433/55 |

*Primary Examiner*—Gene Mancene
*Assistant Examiner*—Nicholas D. Lucchesi
*Attorney, Agent, or Firm*—Lerner, David, Littenberg, Krumholz & Mentlik

[57] ABSTRACT

A maxillary dental arch form is disclosed which enables orientation with a maxillary cast without the use of an articulator, relator or other such instrument. The maxillary dental arch form is provided with incisal pappila and hamular notch engaging members which engage corresponding representations of the incisal pappila and left and right hamular notches within the maxillary cast of the patient's maxillary alveolar ridge. Denture tie-in using conventional wax-up techniques can be quickly accomplished in fabricating partial or full artificial dentures.

37 Claims, 2 Drawing Sheets

DENTAL ARCH FORM

BACKGROUND OF THE INVENTION

The present invention relates in general to a prefabricated dental arch form, and more particularly, to a maxillary arch form having artificial teeth temporarily luted thereto. Still more particularly, the present invention is related to an orientation arrangement that allows the maxillary arch form with artificial teeth to be oriented to the maxillary cast without the use of an instrument such as an articulator or relator.

In the usual method for the construction of artificial dentures, the maxillary and/or mandibular denture is first prepared by placing individual artificial teeth on a base that fits upon a cast of the patient's alveolar ridge which is supported by an articulator or other such instrument. Thereafter, the opposing denture, either the maxillary or mandibular denture, is similarly constructed and may be placed in the patient's mouth to check accuracy and aesthetics during the construction process. One of the drawbacks of these procedures is that the dentures are built up in a piecemeal fashion from individual artificial teeth, with intermediate checks an adjustments.

To this end, there is known from Schwartz, U.S. Pat. No. 4,780,082, prefabricated maxillary and mandibular arch forms having a plurality of teeth temporarily luted thereto which are adapted to maintain the mandibular and maxillary relationship during the fabrication of artificial dentures. An interconnecting arrangement, such as a mating pin and socket is provided on the dental arch forms for interconnecting the mandibular and maxillary members together. As a result, the dentition of the mandibular and maxillary arch forms maintain a predetermined occluded relationship during the fabrication of artificial dentures therefrom. Despite the advantages of the dental arch forms pursuant to Schwartz, there is still the need of the use of a relator and/or an articulator or like instrument for relating the dental arch forms to the maxillary and mandibular casts.

Accordingly, there is a need for a maxillary arch form which is adapted for orienting itself with the maxillary cast of the patient's alveolar ridge without the need of the use of a relator, articulator or the like.

SUMMARY OF THE INVENTION

In accordance with one embodiment of the present invention, there is provided a dental arch form orientable with a maxillary cast having representations of the incisal pappila and hamular notches. The dental arch form is constructed of a maxillary arch-shaped element having a portion for affixing a plurality of teeth thereto, and means attached to the arch-shaped element for orienting the arch shaped element with respect to the maxillary cast by engagement with the representations of the incisal pappila and hamular notches of the maxillary cast.

In accordance with another embodiment of the present invention, there is provided a maxillary dental arch form orientable with a maxillary cast of a person's maxillary alveolar ridge having a representation of the incisal pappila and left and right hamular notches. The maxillary dental arch form is constructed of an arch-shaped element having a plurality of maxillary artificial teeth attached thereto, first means for orienting the maxillary teeth by engagement with the representation of the incisal pappila of the maxillary cast, and second means for orienting the maxillary teeth by engagement with the representations of the left and right hamular notches of the maxillary cast, whereby the plurality of the maxillary teeth are aligned in predetermined relationship with the representation of the maxillary alveolar ridge.

In accordance with another embodiment of the present invention, there is provided dental arch forms for forming dentures therefrom is constructed of a maxillary arch-shaped element orientable with a maxillary cast of a person's maxillary alveolar ridge having a representation of an incisal pappila and left and right hamular notches, the maxillary arch-shaped element having a plurality of artificial maxillary teeth attached thereto, first means for orienting the artificial maxillary teeth by engagement with the representation of the incisal pappila of the maxillary cast, second means for orienting the artificial maxillary teeth by engagement with the representations of the left and right hamular notches of the maxillary cast, a mandibular arch-shaped element having a plurality of artificial mandibular teeth attached thereto, and interconnecting means provided on the maxillary and mandibular arch-shaped elements for interconnecting the arch-shaped elements together in predetermined relationship, whereby the maxillary artificial teeth are aligned and maintained in fixed relationship with the mandibular artificial teeth upon engagement of the interconnecting means.

In accordance with another embodiment of the present invention, there is provided a method of fabricating dentures for a person including the steps of forming a maxillary cast of a person's maxillary alveolar ridge having representations of an incisal pappila and hamular notches, forming a maxillary arch-shaped element having a plurality of artificial teeth attached thereto, orienting the maxillary arch-shaped element with the maxillary cast by engagement with the representations of the incisal pappila and hamular notches, and removing the maxillary arch-shaped element leaving the artificial maxillary teeth secured to the maxillary cast for forming dentures therefrom.

BRIEF DESCRIPTION OF THE DRAWINGS

The above description, as well as further objects, features and advantages of the present invention will be more fully understood with reference to the following detailed description of a dental arch form, when taken in conjunction with the accompanying drawings, wherein.

DETAILED DESCRIPTION

Figure 1:
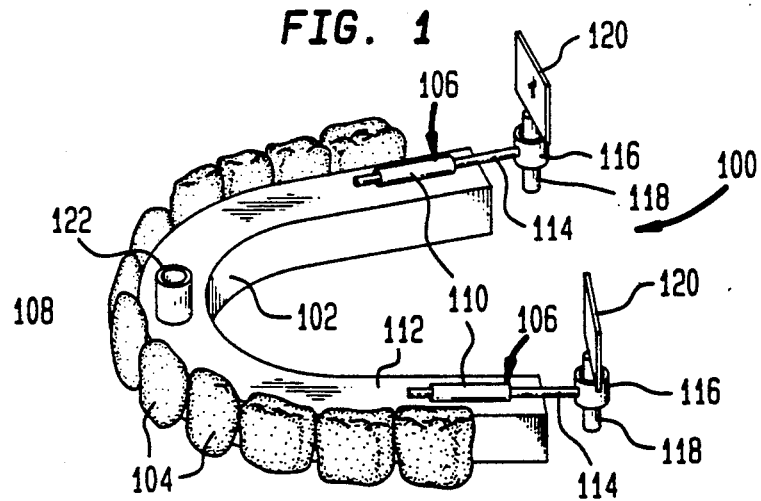
FIG. 1 is a perspective view of a maxillary arch form having orienting members for orienting the arch form with respect to a maxillary cast of a person's alveolar ridge by engagement with representations of the incisal pappila and left and right hamular notches pursuant to one embodiment of the present invention.

Referring now to the drawings, wherein like reference numerals represent like elements, there is disclosed in FIG. 1 a prefabricated maxillary dental arch form generally designated by reference numeral 100. The dental arch form 100 is constructed of a rigid arch-shaped element 102 having a plurality of artificial teeth 104 temporarily luted to the circumferential portion of the element. Although the maxillary dental arch form 100 is shown and described for fabricating full artificial dentures, it is to be understood that such dental arch form has equal utility in fabricating partial dentures and bridges therefrom.

The arch-shaped element 102 is an integral rigid structure, fabricated from any dimensionally stable material such as thermoplastic or thermosetting materials, olefin polymers, e.g., polyethylene, polyvinylchloride, etc. The arch-shaped element 102 may optionally conform to a standard maxillary arch index. The arch-shaped element 102 is preferably anatomically shaped in size to the alveolar ridge of the patient such that, for example, the central fossa of the individual teeth 104 are aligned over the crest of the alveolar ridge. Ordinarily, individual artificial teeth 104 are temporarily attached by, for example, luting to the arch-shaped element 102 to provide a prefabricated maxillary dental arch form 100. All types of cusp teeth, such as steep and flat, may be used and are set in a zero degree plane of occlusion, although a plane of occlusion in the range of from 0–45' is also contemplated.

In accordance with the present invention, the maxillary dental arch form 100 is provided with an orientation system adapted to allow precise direct orientation of the arch-shaped element 102 and luted artificial teeth 104 with the maxillary cast of the alveolar ridge of a patient. Specifically, the arch-shaped element 102 supports a pair of spaced apart hamular notch engagement members 106 and a single incisal pappila engagement member 108. The members 106, 108 as to be described hereinafter, are adapted for engaging representations of the incisal pappila and left and right hamular notches of the maxillary cast formed from the alveolar ridge of the patient.

The hamular notch engagement members 106 are of like construction including a hollow square tubular member 110 affixed to the upper surface 112 of the arch-shaped element 102. An extending square rod 114 is slidingly received within the square tubular members 110 for longitudinal movement in a generally anterior and posterior direction without rotation. One free end of square rod 114 supports a socket 116 which rotatably receives a vertical shaft 118 to which there is affixed a flat, rectangular shaped blade 120. Based upon the foregoing construction, the blade 120 may be rotated about a vertical axis extending through shaft 118, as well as being displaced anteriorly and posteriorly by sliding movement of square rod 114 within square tubular member 110. A single elongated blade 120 may be used extending between and connected to the spaced vertical shafts 118.

The incisal pappila engagement member 108 as constructed pursuant to one embodiment includes a hollow tube 122, shown enlarged for clarity, attached to the arch-shaped element 102 at the midline which extends through the center of the region of incisal pappila and centrally between the left and right hamular notches. The tube 122 is constructed to receive an elongated pin 124, see FIG. 4, which is mounted in the representation of the incisal pappila of the maxillary cast. In accordance with one embodiment, the height of tube 122 and blades 120 are approximately 15 mm high each, resulting in a zero degree plane with respect to a plane extending through the representation of the incisal pappila and left and right hamular notches of the maxillary cast. However, it is to be understood that the height of the tube 122 or blades 120 may be varied so as to produce planes of other than zero degrees if desired.

Figure 2:
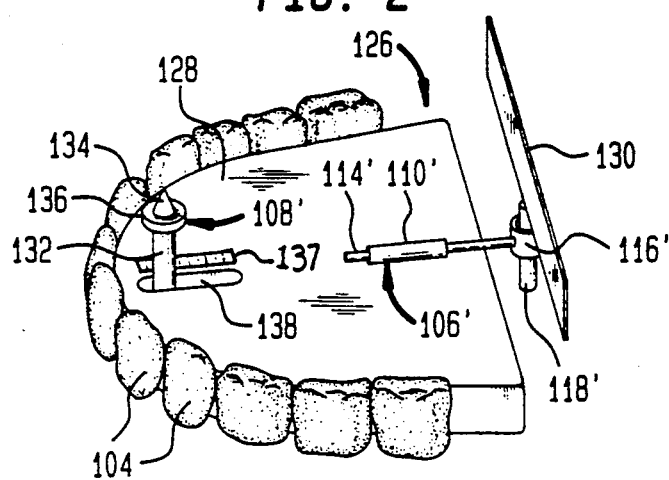
FIG. 2 is a perspective view of a maxillary arch form constructed in accordance with another embodiment of the present invention.

Referring now to FIG. 2, there is illustrated a maxillary dental arch form 126 constructed in accordance with another embodiment of the present invention. The maxillary dental arch form 126 is constructed of a rigid D-shaped element 128 and a plurality of artificial teeth 104 temporarily luted to the circumferential portion of the element. The D-shaped element 128 is constructed of similar materials and in a similar manner as the arch-shaped element 102 described with respect to the maxillary dental arch form 100. The D-shaped element 128 supports a single hamular notch engagement member 106' positioned along the midline as previously defined. The hamular notch engagement member 106' differs from that previously described in that there is provided a single elongated rectangular blade 130 of sufficient length to simultaneously engage the representations of the right and left hamular notches of the maxillary cast. In all other respects, the hamular notch engagement member 106', as thus far described, is of similar construction to members 106 and operated in a similar manner.

The incisal pappila engagement member 108' is constructed as an elongated solid rod 132 having a pointed end 134 surrounded by a stop collar 136. The rod 132 is slidably mounted within an elongated slot 138 within the D-shaped element 128. This arrangement enables movement of the incisal pappila engagement member 108' anteriorly and posteriorly along the midline as previously defined. A similar arrangement can be provided for the tube 122 as shown in FIG. 1 to allow for its movement anteriorly and posteriorly. A millimeter scale 137 may be provided adjacent the elongated slot 138 to determine the anterior or posterior position of the teeth. A millimeter scale 137 can also be provided adjacent tube 122 when constructed to be movable for a similar purpose.

In accordance with one embodiment, the height of rod 132 and blade 130 are approximately 15 mm high each, resulting in a zero degree plane with respect to a plane extending through the representation of the incisal pappila and left and right hamular notches of the maxillary cast. However, it is to be understood that the height of the rod 132 or blade 130 may be varied so as to produce planes of other than zero degrees if desired.

Figure 3:
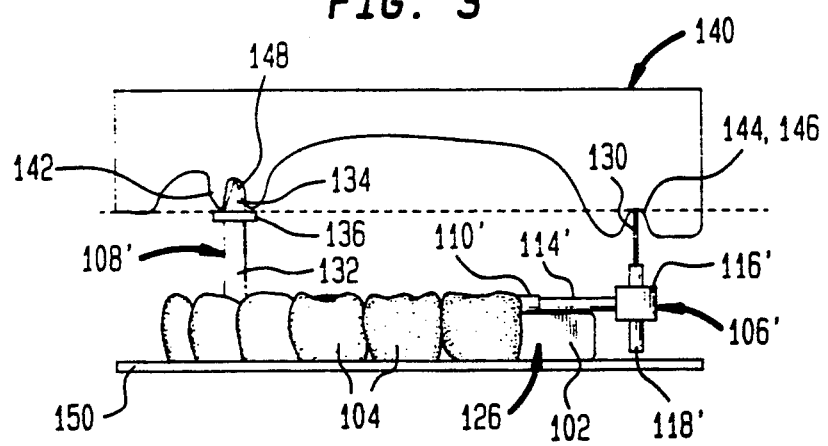
FIG. 3 is a side elevational view showing the orientation of the maxillary arch form as shown in FIG. 2 with the representations of the incisal pappila and left and right hamular notches of the maxillary cast of a patient's alveolar ridge.
Figure 4:
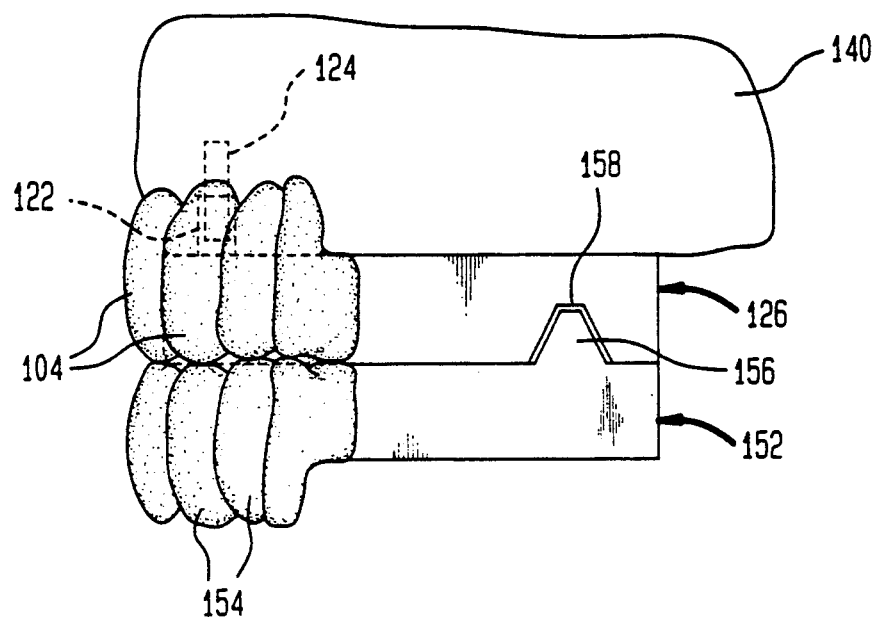
FIG. 4 is a side elevational view of maxillary and mandibular arch forms interconnected in an arrangement to maintain a predetermined occluded relationship in preparing dentures pursuant to the present invention.

There will now be described the fabrication of full or partial dentures pursuant to the present invention using casts that are representative of the patient's mandibular and maxillary alveolar ridges. The fabrication of the maxillary set up using a maxillary dental arch form 126 will be described with reference to FIG. 3. Initially, a representation is taken of the maxillary and mandibular alveolar ridges of the patient in order to fabricate a corresponding maxilla and mandibular cast, for example, in the manner disclosed in U.S. Pat. No. 4,235,594, also issued to the inventor of the subject matter of this application. A maxillary cast 140 is formed with representations of the incisal pappila 142 and left and right hamular notches 144, 146. In the embodiment illustrated, the representation of the incisal pappila 142 is provided with an opening 148, as opposed to pin 124 as shown in FIG. 4. A prefabricated maxillary dental arch form 126 is selected to conform most closely to the patient's actual arch size, i.e., anatomically correct. The actual arch size is determined using arch key and standard maxillary arch indexes such as Hawley Arch Charts and other orthodontic arch charts, as well as Pont's Index. In this regard, the selected fabricated maxillary dental arch form 126 will place the central fossae of the maxillary teeth 104 over the maxillary alveolar ridge.

The maxillary dental arch form 126 may positioned on a support table 150 or held in one's hand. The maxillary cast 140 is positioned overlying the maxillary dental arch form 126 such that the pointed end 134 of the incisal pappila engagement member 108' is received within the opening 148 within the representation of the incisal pappila 142. The extent of engagement is limited by the stop collar 136. As shown in FIG. 4, the opening 148 may be replaced with a pin 124 to be received within the hollow tube 122 pursuant to the maxillary dental arch form 100 illustrated and described with respect to FIG. 1.

In a similar manner, blade 130 of the hamular notch engagement member 106' is positioned to simultaneously engage the representations of the left and right hamular notches 144, 146. Alignment is achieved by rotating the blade 130 via shaft 118' within socket 116' and displacing the blade anteriorly or posteriorly by means of rod 114'. Where the maxillary dental arch form 100 pursuant to FIG. 1 is employed, the two spaced apart blades 120 are individually aligned for engagement with the representations of the left and right hamular notches 144, 146 in a similar manner as thus far described. As the D-shaped element 128 may be moved anteriorly or posteriorly with respect to the hamular notch engagement member 106' via shaft 118' and incislar pappila engagement 108' via slot 138, the central fossa of the maxillary teeth 104 may be accurately positioned over the maxillary alveolar ridge. Once aligned, the maxillary dental arch form 126 is waxed to the maxillary cast 140 to the desired thickness.

Referring to FIG. 4, a prefabricated mandibular dental arch form 152 having a plurality of mandibular artificial teeth 154 temporarily luted thereto is constructed in a similar manner as the maxillary dental arch forms 100, 126. The mandibular dental arch form 152 is constructed without the incisal pappila and hamular notch engagement members 106, 108. The prefabricated mandibular dental arch form 152 is interconnected to the prefabricated maxillary dental arch form 126 by means of interconnecting members which include a projecting pin 156 or other such member extending upwardly from the mandibular dental arch form and a receiving socket 158 within the maxillary dental arch form. The pin 156 and socket 158 combination are sized for releasable engagement to permit temporarily interconnecting of the maxillary and mandibular set up formed from the maxillary and mandibular dental arch forms 126, 152 during denture fabrication. The pin 156 and socket 158 combination are provided at a plurality of spaced locations, preferably three arranged in a triangle, within the maxillary and mandibular dental arch forms 126, 152 in a manner as disclosed in Schwartz, U.S. Pat. No. 4,780,082. The pin 156 and socket 158 combination may be provided in a lesser or greater number than that disclosed, as well as being provided in other than a triangular relationship. To this end, the purpose of the pin 156 and socket 158 combination is to maintain a predetermined relationship between the artificial teeth temporarily luted to the maxillary and mandibular dental arch forms 126, 152.

As shown, the interconnected maxillary and mandibular dental arch forms 126, 152 form a mandibular and maxillary setup having a predetermined maxillary occlusal relationship. Although the interconnecting members have been described as a pin 156 and a receiving socket 158, it is to be understood that other members and devices adapted for interconnecting a maxillary and mandibular dental arch form 126, 152 are contemplated.

The maxillary and mandibular dental arch forms 126, 152 are interconnected to maintain a predetermined occlusion whereby their maxilo-mandibular relationship provides a natural dentition and the proper labial drape. The mandibular dental arch form 152 is similarly waxed to a mandibular cast (not shown) to the desired thickness. Minor changes may now be made to the maxillary and mandibular dental arch forms 126, 152 prior to further processing. For example, the individual artificial teeth 104, 154 may be adjusted by, for example, tilting and angling the teeth according to the dictates of good aesthetics. The resulting maxillary and mandibular dentures are completed after removal of elements 102, 128, using conventional processes, such as flasking and milling, followed by decasting and polishing.

Although the invention herein has been described with reference to particular embodiments, it is to be understood that these embodiments are merely illustrative of the principles and application of the present invention. In particular, it is noted that the present invention is useful in fabrication of full or partial dentures having flat plane occlusion, curve of Spee or curve of Wilson. The present invention will allow the manufacture of dental teeth to supply same preset up. It is therefore to be understood that numerous modifications may be made in the illustrative embodiments and that other arrangements may be devised without departing from the spirit and scope of the present invention as defined by the appended claims.

What is claimed is:

1. A dental arch form orientable directly with a maxillary cast having representations of an incisal pappila and hamular notches, said dental arch form comprising a maxillary arch-shaped element having a portion for affixing a plurality of teeth thereto, a plurality of artificial maxillary teeth attached to a circumferential portion of said maxillary arch-shaped element, and means attached to said arch-shaped element for orienting said arch-shaped element with respect to the maxillary cast, said means including portions located for engagement with the representations of the incisal pappila and hamular notches on the maxillary cast.

2. The dental arch form of claim 1, further including a mandibular arch-shaped element having a portion for affixing a plurality of artificial mandibular teeth thereto, and interconnecting means provided on said maxillary and mandibular arch-shaped elements for interconnecting said arch-shaped elements together in predetermined relationship.

3. The dental arch form of claim 1, wherein said means comprises a first member for engaging the representation of the incisal pappila and a second member for engaging the representations of the hamular notches.

4. The dental arch form of claim 3, wherein said first member comprises a solid rod.

5. The dental arch form of claim 4, wherein the representation of the incisal pappila includes a hole, and said rod includes stop means for limiting the depth of insertion of said rod into said hole.

6. The dental arch form of claim 3, wherein said first member is movable anteriorly and posteriorly along a midline of said arch-shaped element to enable alignment of a circumferential portion of said arch-shaped element with a representation of the maxillary alveolar ridge of the maxillary cast.

7. The dental arch form of claim 3, wherein said second member comprises a blade having a portion for engaging the representations of the hamular notches.

8. The dental arch form of claim 7, further including means for enabling rotation of said blade about an axis thereof.

9. The dental arch form of claim 7, further including means for enabling moving said blade anteriorly and posteriorly along said maxillary arch-shaped element.

10. The dental arch form of claim 7, further including a pair of spaced apart blades for individually engaging the representations of the hamular notches.

11. The dental arch form of claim 3, wherein said first member comprises a hollow tube for receiving a pin, said pin securable within a maxillary cast having the representation of an incisal pappila.

12. The dental arch form of claim 3, wherein said first member comprises a hollow tube.

13. The dental arch form of claim 1, wherein said means comprises a first member for engaging the representation of the incisal pappila and a second member for engaging the representation of the hamular notches, said second member moveable relative to said dental arch form for alignment within said hamular notches.

14. A maxillary dental arch form orientable with a maxillary cast of a person's maxillary alveolar ridge having a representation of an incisal pappila and left and right hamular notches, said maxillary dental arch form comprising an arch-shaped element having a plurality of maxillary artificial teeth attached thereto, first means for orienting said maxillary teeth by engagement with the representation of the incisal pappila of the maxillary cast, and second means movable relative to said dental arch form for orienting said maxillary teeth by engagement with the representations of the left and right hamular notches of said maxillary cast, whereby said plurality of said maxillary teeth are aligned in predetermined relationship with the representation of the maxillary alveolar ridge.

15. The dental arch form of claim 14, wherein said maxillary arch-shaped element is U-shaped.

16. The dental arch form of claim 14, further including a mandibular arch-shaped element having a plurality of artificial mandibular teeth attached thereto, and interconnecting means providing on said maxillary and mandibular arch-shaped elements for interconnecting said arch-shaped elements together in predetermined orientation.

17. The dental arch form of claim 14, wherein said first means comprises a first member for engaging the representation of the incisal pappila and said second means comprising a second member for separately or commonly engaging the representations of left and right hamular notches.

18. The dental arch form of claim 14, wherein said first means comprises a solid rod.

19. The dental arch form of claim 18, wherein the representation of the incisal pappila includes a hole therein, and said rod includes stop means for limiting the depth of insertion of said rod into said hole.

20. The dental arch form of claim 14, wherein said first means is movable anteriorly and posteriorly along a midline of said arch-shaped element to enable alignment of a circumferential portion of said arch-shaped element with a representation of the maxillary alveolar ridge of the maxillary cast.

21. The dental arch form of claim 14, wherein said second means comprises a blade having a portion for engaging the representations of the right and left hamular notches.

22. The dental arch form of claim 21, further including means for enabling rotation of said blade about an axis thereof.

23. The dental arch form of claim 22, further including means for enabling moving said blade anteriorly and posteriorly along said maxillary arch-shaped element.

24. The dental arch form of claim 21, further including a pair of spaced apart blades for individually engaging the representations of the left and right hamular notches.

25. The dental form of claim 14, wherein said first member comprises a hollow tube for receiving a pin, said pin securable within a maxillary cast having the representation of an incisal pappila.

26. Dental arch forms for forming dentures therefrom comprising a maxillary arch-shaped element orientable with a maxillary cast of a person's maxillary alveolar ridge having representations of an incisal pappila and left and right hamular notches, said maxillary arch-shaped element having a plurality of artificial maxillary teeth attached thereto, first means for orienting said artificial maxillary teeth by engagement with the representation of the incisal pappila of said maxillary cast, second means for orienting said artificial maxillary teeth by engagement with the representations of the left and right hamular notches of said maxillary cast, a mandibular arch-shaped element having a plurality of artificial mandibular teeth attached thereto, and interconnecting means provided on said maxillary and mandibular arch-shaped elements for interconnecting said arch-shaped elements together in predetermined relationship, whereby said maxillary artificial teeth are aligned and maintained in fixed relationship with said mandibular artificial teeth upon engagement of said interconnecting means.

27. The dental arch forms of claim 26, wherein said first means comprises a solid rod.

28. The dental arch forms of claim 26, wherein said second means comprises a blade having a portion for engaging the representations of the right and left hamular notches, said blade rotatable about an axis thereof and moveable anteriorly and posteriorly along said maxillary arch-shaped element.

29. The dental arch form of claim 26, wherein said first means comprises a hollow tube.

30. A method of fabricating dentures for a person comprising the steps of forming a maxillary cast of a person's maxillary alveolar ridge having representations of an incisal pappila and hamular notches, forming a maxillary arch-shaped element having a plurality of artificial teeth attached thereto, orienting said maxillary arch-shaped element with said maxillary cast by engagement with the representations of the incisal pappila and hamular notches, and removing said maxillary arch-shaped element leaving said artificial maxillary teeth secured to said maxillary cast for forming dentures therefrom.

31. The method as set forth in claim 30, further including forming a mandibular arch-shaped element having a plurality of artificial teeth attached thereto, interconnecting said mandibular arch-shaped element to said maxillary arch-shaped element so as to maintain the occluded relationship and to prevent relative movement between said artificial maxillary and mandibular teeth, mounting said mandibular arch-shaped element to a mandibular cast of a person's mandibular alveolar ridge, and removing said mandibular arch-shaped element leaving said artificial mandibular teeth secured to said mandibular cast for forming dentures therefrom.

32. A dental arch form orientable with a maxillary cast having representations of an incisal pappila and hamular notches, said dental arch form comprising a maxillary arch-shaped element having a portion for affixing a plurality of teeth thereto, a plurality of artificial maxillary teeth attached to a circumferential portion of said maxillary arch-shaped element, and means attached to said arch-shaped element for orienting said arch-shaped element with respect to the maxillary cast, said means comprising a first member for engaging the representation of the incisal pappila and a second member comprising a blade having a portion for engaging the representations of the hamular notches.

33. The dental arch form of claim 32, further including means for enabling rotation of said blade about an axis thereof, and means for enabling moving said blade anteriorly and posteriorly along said maxillary arch-shaped element.

34. A maxillary dental arch form orientable with a maxillary cast of a person's maxillary alveolar ridge having a representation of an incisal pappila and left and right hamular notches, said maxillary dental arch form comprising an arch-shaped element having a plurality of maxillary artificial teeth attached thereto, first means for orienting said maxillary teeth by engagement with the representation of the incisal pappila of the maxillary cast, and second means comprising a blade having a portion for orienting said maxillary teeth by engagement with the representations of the left and right hamular notches of said maxillary cast, whereby said plurality of said maxillary teeth are aligned in predetermined relationship with the representation of the maxillary alveolar ridge.

35. The dental arch form of claim 34, further including means for enabling rotation of said blade about an axis thereof, and means for enabling moving said blade anteriorly and posteriorly along said maxillary arch-shaped element.

36. A dental arch form orientable directly with a maxillary cast having representations of an incisal papilla and hamular notches, said dental arch form comprising a maxillary arch-shaped element having locations for affixing a plurality of teeth thereto, and orientation means attached to said arch-shaped element for orienting said arch-shaped element with respect to the maxillary cast, said orientation means including elements located for engagement with the representations of the incisal papilla and hamular notches on the maxillary cast, said locations for affixing said plurality of teeth aligning directly with respect to the maxillary cast when said elements of said orientation means simultaneously engage said representations of the incisal papilla and hamular notches on the maxillary cast.

37. The dental arch form of claim 36, wherein said maxillary cast further includes representation of a maxillary alveolar ridge, said locations for affixing said plurality of teeth being aligned therewith.

* * * * *